(12) United States Patent
Hayashi et al.

(10) Patent No.: US 7,897,811 B2
(45) Date of Patent: Mar. 1, 2011

(54) PROCESS FOR PRODUCTION OF RADIOACTIVE FLUORINE-LABELED ORGANIC COMPOUND

(75) Inventors: Akio Hayashi, Sodegaura (JP); Fumie Kurosaki, Sodegaura (JP); Masahito Toyama, Sodegaura (JP); Toshiyuki Shinmura, Sodegaura (JP); Emi Kaneko, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 295 days.

(21) Appl. No.: 12/227,240

(22) PCT Filed: May 7, 2007

(86) PCT No.: PCT/JP2007/059459

§ 371 (c)(1),
(2), (4) Date: Nov. 12, 2008

(87) PCT Pub. No.: WO2007/132689

PCT Pub. Date: Nov. 22, 2007

(65) Prior Publication Data

US 2009/0198085 A1 Aug. 6, 2009

(30) Foreign Application Priority Data

May 11, 2006 (JP) .............................. 2006-132089

(51) Int. Cl.
*C07C 61/04* (2006.01)
(52) U.S. Cl. ...................................... 562/505
(58) Field of Classification Search ........................ None
See application file for complete search history.

(56) References Cited

U.S. PATENT DOCUMENTS

| 2006/0039855 A1 | 2/2006 | Gibson et al. |
| 2007/0036258 A1 | 2/2007 | Ito et al. |

FOREIGN PATENT DOCUMENTS

| JP | 2006-510706 | 3/2006 |
| WO | WO2004/056725 | 7/2004 |
| WO | WO2005/030677 | 4/2005 |

OTHER PUBLICATIONS

PCT International Preliminary Report on Patentability in PCT/JP2007/059459, dated Dec. 10, 2008.
PCT Written Opinion of the International Searching Authority in PCT/JP2007/069459.

*Primary Examiner*—Paul A Zucker
(74) *Attorney, Agent, or Firm*—Fitch, Even, Tabin & Flannery

(57) ABSTRACT

A process is provided for producing [$^{18}$F]FACBC, which can reduce the production amount of impurities. Disclosed is a process for producing a radioactive fluorine-labeled organic compound, including a deesterification step of retaining, in a reverse-phase column, a compound represented by Formula (1):

(1)

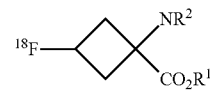

wherein $R^1$ is a linear or branched $C_1$-$C_{10}$-alkyl chain or an aromatic substituent, and $R^2$ is a protecting group;
charging the column with an alkaline solution to deesterify the compound, and subsequently discharging the alkaline solution from the column to obtain a compound represented by Formula (2):

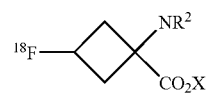

wherein X is sodium or potassium; and
a deprotection step of deprotecting the amino-protecting group of the compound obtained in the deesterification step to obtain a compound represented by Formula (3):

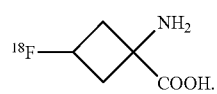

5 Claims, 1 Drawing Sheet

PROCESS FOR PRODUCTION OF RADIOACTIVE FLUORINE-LABELED ORGANIC COMPOUND

CROSS-REFERENCE TO RELATED APPLICATIONS

This is a U.S. National Phase of International Application PCT/JP2007/059459, filed May 7, 2007, and claims the benefit of foreign priority under 35 U.S.C. §119 based on JP 2006-132089, filed May 11, 2006, the entire disclosures of which applications are hereby incorporated herein by reference.

TECHNICAL FIELD

The present invention relates to a process for production of a radioactive fluorine-labeled organic compound. More particularly, the invention relates to a process for production of a radioactive fluorine-labeled organic compound useful in detecting tumors by positron emission tomography.

BACKGROUND ART

Nuclear medicine examination represented by positron emission tomography (hereinafter referred to as PET) and single photon emission computed tomography (hereinafter referred to as SPECT), is effective in diagnosing a variety of diseases including heart disease and cancer. These techniques involve administering an agent labeled with a specific radioisotope (hereinafter referred to as radiopharmaceutical) to a patient, followed by detecting γ-rays emitted directly or indirectly from the agent. Nuclear medicine examination is characteristic in that it has not only high specificity and sensitivity to diseases, but also an advantage of providing information on the functionality of lesions, compared to other examination techniques.

For example, [$^{18}$F]2-fluoro-2-deoxy-D-glucose (hereinafter referred to as "[$^{18}$F]-FDG"), one of radiopharmaceuticals used for PET examination, tends to be concentrated in areas where glucose metabolism is enhanced, thereby making it possible to specifically detect tumors in which glucose metabolism is enhanced.

Nuclear medicine examination is performed by tracing a distribution of an administered radiopharmaceutical, and data obtained therefrom vary depending on nature of the radiopharmaceutical. Thus, different radiopharmaceuticals have been developed for different diseases, and some of them are put into clinical use. There have been developed, for example, various tumor diagnostic agents, bloodstream diagnostic agents and receptor mapping agents.

In recent years, a series of radioactive halogen-labeled amino acid compounds including [$^{18}$F]1-amino-3-fluorocyclobutanecarboxylic acid (hereinafter referred to as [$^{18}$F]FACBC) have been designed as novel radiopharmaceuticals, and their clinical application is under examination (Patent Document 1, and non-Patent Documents 1 and 2). [$^{18}$F]FACBC is considered to be effective as a diagnostic agent for highly proliferative tumors, because it has a property of being taken up specifically by amino acid transporter.

As processes for producing [$^{18}$F]FACBC, there are disclosed processes which include: providing 1-(N-(t-butoxycarbonyl)amino)-3-[((trifluoromethyl)sulfonyl)oxy]-cyclobutane-1-carboxylic acid ester as a labeling precursor, substituting the triflate group at position 3 of the precursor with radioactive fluorine, and carrying out elimination reactions of the esterified group and the Boc group by subjecting the resulting compound in a form of a solution to an acidic condition (Patent Document 1, and non-Patent Documents 1 and 2).

For the production of [$^{18}$F]-FDG, a synthetic process wherein deprotection step is performed in a solid phase is disclosed, which enables a shortened synthetic time, a reduced number of reagents, and a reduced number of components in the manufacturing apparatus (Patent Document 2).

Patent Document 1: Japanese Patent Laid-Open No. 2000-500442.

Patent Document 2: Japanese Patent Laid-Open No. 11-508923.

Non-Patent Document 1: Jonathan McConathy et al., "Improved synthesis of anti-[$^{18}$F]FACBC: improved preparation of labeling precursor and automated radiosynthesis.", Applied Radiation and Isotopes, (Netherlands), 2003, 58, p. 657-666.

Non-Patent Document 2: Timothy M. Shoup et al., "Synthesis and Evaluation of [$^{18}$F]1-Amino-3-fluorocyclobutane-1-carboxylic Acid to Image Brain Tumors.", The Journal of Nuclear Medicine, 1999, 40, p. 331-338.

DISCLOSURE OF THE INVENTION

Problems to be Solved by the Invention

The processes for producing [$^{18}$F]FACBC thus far disclosed have achieved production yields of from 12 to 24% (J. McConathy et al., Applied Radiation and Isotopes, 2003, 58, p. 657-666), which cannot be regarded as being sufficiently high from the standpoint of industrial production. That is to say, in order to industrially produce [$^{18}$F]FACBC, it is desirable to use a production process or condition that can stably provide a higher yield.

The production of [$^{18}$F]FACBC mainly includes a radiofluorination step in which radioactive fluorine is added to a labeling precursor; and a deesterification and deprotection step in which the intermediate compound produced in the radiofluorination step is deesterified and deprotected. The present inventors conducted a study on the radiofluorination step in order to improve the production yield, and established a technique whereby the yield of the fluorination step can be improved up to 73.79%, which had been 24.16% according to conventional processes. Consequently, the inventors made it possible to improve the production yield of [$^{18}$F]FACBC up to 54.8±4.8% (N=15). However, a detailed study conducted by the inventors revealed that the resulting aqueous [$^{18}$F]FACBC solution contained a large amount of non-radioactive impurities (see the Comparative Examples described below). The amount of impurities in pharmaceuticals must be suppressed to a certain level or lower. Thus, if impurities are present at the certain level or higher after the completion of the reaction, the impurities must be removed in the subsequent step. However, the addition of a further purification step for reducing impurities causes prolongation of the time required for the production steps subsequent to the radioactive fluorine labeling. Because the half-life of radioactive fluorine is as short as about 110 minutes, it is not preferable to prolong the time required for the steps after the radioactive fluorine labeling from the viewpoint of industrial production of radioactive fluorine-labeled compounds.

The present invention has been made in view of the above-described circumstances, and has aimed to provide a process for production of [$^{18}$F]FACBC, which can reduce the production amount of non-radioactive impurities.

Means for Solving the Problems

As a result of investigations, the inventors have found that the amount of impurities in a target product can be easily and effectively reduced by performing the deesterification step of the ester group, that is, a carboxyl-protecting group in a reverse-phase solid-phase column, and thus have accomplished the present invention. The solid-phase deprotection method has conventionally been employed for the purpose of mainly reducing the production time (see, for example, Japanese Patent Laid-Open No. 11-508923). The inventors have found that the use of the solid-phase deprotection method can achieve a new effect of reducing the amount of impurities present in a target product, and have applied this finding.

In accordance with the present invention, there is provided a process for production of a radioactive fluorine-labeled organic compound, comprising a deesterification step of retaining, in a reverse-phase column, a compound represented by the following formula (1):

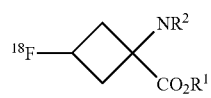
(1)

wherein $R^1$ is a linear or branched $C_1$-$C_{10}$ alkyl chain or an aromatic substituent; and $R^2$ is a protecting group;

charging the column with an alkaline solution to deesterify the above compound, and subsequently discharging the alkaline solution from the column to obtain a compound represented by the following formula (2):

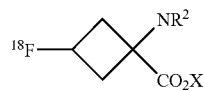
(2)

wherein X is sodium or potassium; and $R^2$ is a protecting group;

and a deprotection step of deprotecting the amino-protecting group of the compound obtained in the deesterification step to obtain a compound represented by the following formula (3):

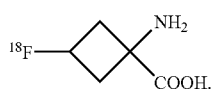
(3)

In the formulas shown above, $R^1$ is a linear or branched $C_1$-$C_{10}$ alkyl chain or an aromatic substituent, and is preferably a substituent selected from methyl, ethyl, t-butyl, and phenyl groups.

In the formulas shown above, $R^2$ is a protecting group, and is not particularly limited as long as it can prevent the reaction between the radioactive fluorine and the amino group. Specifically, a protecting group selected from the group consisting of various carbamate substituents, various amide substituents, various imide substituents, and various amine substituents can be used. Preferably, a protecting group selected from the group consisting of linear or branched $C_2$-$C_7$ alkyloxycarbonyl substituents; linear or branched $C_3$-$C_7$ alkenyloxycarbonyl substituents; $C_7$-$C_{12}$ benzyloxycarbonyl substituents that may have a modifying group; $C_2$-$C_7$ alkyldithiooxycarbonyl substituents; linear or branched $C_1$-$C_6$ alkylamide substituents; linear or branched $C_2$-$C_6$ alkenylamide substituents; $C_6$-$C_{11}$ benzamide substituents that may have a modifying group; $C_4$-$C_{10}$ cyclic imide substituents; $C_6$-$C_{11}$ aromatic imine substituents that may have a substituent; linear or branched $C_1$-$C_6$ alkylamine substituents; linear or branched $C_2$-$C_6$ alkenylamine substituents; and $C_6$-$C_{11}$ benzylamine substituents that may have a modifying group can be used. More preferably, a protecting group selected from t-butoxycarbonyl group, allyloxycarbonyl group, phthalimide group, and N-benzylideneamine substituent can be used; and most preferably, t-butoxycarbonyl group or phthalimide group can be used.

In the formulas shown above, X is a cation contained in the alkali used in the deesterification step, and is selected according to the type of the alkali. For example, with sodium hydroxide, X is sodium, and with potassium hydroxide, X is potassium.

In the deesterification step, various columns with packing whose functional groups are hydrophobic groups such as phenyl, cyclohexyl and alkyl groups can be used as the reverse-phase column. Preferably used is a reverse-phase column with packing having a structure in which a $C_2$-$C_{18}$ alkyl chain is attached via silicon to a support. A specific example of the reverse-phase column includes one having octadecylsilyl groups as the functional group.

The retention of the compound of the above formula (1) in the reverse-phase column can be performed by various methods. Specifically, a method can be used in which a solution of the compound of the above formula (1) obtained by the radiofluorination step is diluted with water, and the resulting solution is passed through the reverse-phase column. Water for the dilution may be used in an amount sufficient to immobilize the compound of the above formula (1) on the reverse-phase column.

As the alkaline solution, various ones may be used, but a sodium hydroxide solution is preferably used. The amount of the alkaline solution to be used is preferably equal to or greater than the filling capacity of the solid-phase column. The concentration of the alkaline solution is not limited as long as the alkali can be introduced into the column in an amount sufficient to perform deesterification; care must be taken, however, because if the amount thereof is too much, it will be necessary to use a larger amount of acid in the subsequent deprotection step. In the deesterification step, the reverse-phase column is kept for a certain period of time retaining the compound of the above formula (1) while being charged with the alkaline solution. The time in which the reverse-phase column is kept being charged with the alkaline solution is not particularly limited as long as it is sufficient to perform the deesterification reaction.

When the alkaline solution is discharged from the column, the compound represented by the above formula (2) is discharged together with the alkaline solution. At the time, water may be further passed through the column after the discharge of the alkaline solution, so as to wash out any residual compound (2). This wash-out operation can further improve the yield of the compound (2).

The deprotection step can be carried out by use of known methods, for example, a method described in a literature "J. McConathy et al., Applied Radiation and Isotopes, 2003, 58, p. 657-666"; and specifically, a method in which an acidic condition is imparted to the reaction solution after the deesterification step has been completed.

The radiofluorination step can be carried out by use of a known method or a combination of a known method with a condition that we have established. Specifically, a compound represented by the following formula (4):

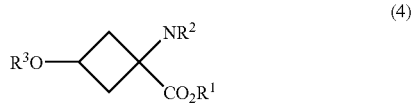
(4)

and an inert organic solvent are added to the mixture containing a phase transfer catalyst with $^{18}$F ions and potassium ions so as to prepare a reaction solution, and a reaction condition such as heating while stirring is applied to the reaction solution.

In the formula (4), $R^1$ and $R^2$ are as defined above; $R^3$ is a member selected from the group consisting of linear or branched $C_1$-$C_{10}$ haloalkyl sulfonic acid substituents; linear or branched $C_1$-$C_{10}$ alkyl sulfonic acid substituents; fluorosulfonic acid substituents; and aromatic sulfonic acid substituents. A substituent selected from methanesulfonic acid, toluenesulfonic acid, nitrobenzenesulfonic acid, benzenesulfonic acid, trifluoromethanesulfonic acid, fluorosulfonic acid, and perfluoroalkylsulfonic acid can be preferably used.

In the radiofluorination step, various inert organic solvents may be used, but an amphiphilic organic solvent should be used. Specifically, a solvent selected from the group consisting of tetrahydrofuran, 1,4-dioxane, acetone, dimethylformamide, dimethylsulfoxide, and acetonitrile can be used, with acetonitrile being particularly preferable. The amount of the inert organic solvent to be used is preferably adjusted so that the labeling precursor concentration in the reaction solution under the radiofluorination reaction is 40 mmol/L or more, in order to significantly improve the yield in the radiofluorination reaction.

Various conditions can be used as the reaction condition for the radiofluorination step; for example, a condition in which the reaction solution is heated while stirring can be used. The heating temperature in this case must not be higher than the evaporation temperature of the inert organic solvent added to the reaction solution; for example, when acetonitrile is used as the inert organic solvent, the heating temperature can be from 70 to 90° C.

EFFECTS OF THE INVENTION

The production process of the present invention is capable of reducing the amount of non-radioactive impurities produced in the production of radioactive fluorine-labeled amino acid compounds such as [$^{18}$F]FACBC, and is also useful as a process for purifying such radioactive fluorine-labeled amino acid compounds.

BEST MODE FOR CARRYING OUT THE INVENTION

Hereinafter, the process for production of a radioactive fluorine-labeled amino acid according to the invention is described in detail.

In the most preferred embodiment, the production process of the present invention includes the steps of (1) reacting a labeling precursor with a mixture containing a phase transfer catalyst, $^{18}$F ions, and potassium ions to label the labeling precursor with radioactive fluorine, thereby producing a radioactive fluorine-labeled precursor ester (a radiofluorination step); (2) deesterifying the radioactive fluorine-labeled precursor ester in a solid-phase column (a deesterification step); and (3) deprotecting the amino-protecting group of the compound obtained in the deesterification step (a deprotection step).

Radioactive fluorine can be obtained by a known method, for example, a method in which $H_2^{18}O$ enriched water is used as a target and exposed to proton bombardment. In this instance, radioactive fluorine exists in the $H_2^{18}O$ enriched water used as a target. The $H_2^{18}O$ enriched water containing radioactive fluorine is allowed to pass through an anion-exchange column so that the radioactive fluorine is adsorbed and collected on the column, thereby being separated from the $H_2^{18}O$ enriched water. Thereafter, a potassium carbonate solution is allowed to pass through the column to elute the radioactive fluorine, and the eluate is supplemented with a phase transfer catalyst and is evaporated to dryness to obtain a mixture containing the phase transfer catalyst as well as $^{18}$F ions and potassium ions.

The amount of potassium carbonate to be used here as potassium ion may be equivalent to or greater than the amount of the labeling precursor used in the subsequent radiofluorination step; however, an excessive amount of potassium carbonate is not preferable because the reaction product may decompose by the influence of carbonate ions. In the most preferred embodiment, concentration and amount of the potassium carbonate solution are adjusted so that the amount of potassium ion is made about equivalent to that of the labeling precursor.

Various compounds having a property to form a clathrate with $^{18}$F ion may be used as a phase transfer catalyst. Specifically, various compounds used for production of radioactive fluorine-labeled organic compounds may be used; 18-crown-6-ether and other various aminopolyethers may be used. In the most preferable embodiment, 4,7,13,16,21,24-hexaoxa-1,10-diazabicyclo[8.8.8]hexacosane can be used.

The larger the amount of the phase transfer catalyst is, the higher the yield will become; but an excessive amount is not preferable because the removal of the excessively-added phase transfer catalyst will often be insufficient. In a preferred embodiment, the total amount of the phase transfer catalyst may be 0.2 mmol or less; for example, when the amount of the labeling precursor to be used is 80 μmol, the molar ratio of the phase transfer catalyst to the labeling precursor is 2.5 or less.

After the mixture containing the phase transfer catalyst as well as $^{18}$F ions and potassium ions has been obtained, radiofluorination is performed by reacting a labeling precursor and $^{18}$F ions. Various methods can be used for the radiofluorination step; for example, a method can be used in which 1-(N-(t-butoxycarbonyl)amino)-3-[((trifluoromethyl)sulfonyl)oxy]-cyclobutane-1-carboxylic acid ethyl ester and an inert organic solvent are added to the above-mentioned mixture to prepare a reaction solution, and then a reaction condition such as heating while stirring is imparted to the reaction solution to produce [$^{18}$F]1-(N-(t-butoxycarbonyl)amino)-3-fluorocyclobutane-1-carboxylic acid ethyl ester (hereinafter referred to as "[$^{18}$F]Boc-FACBC"). In the most preferred embodiment, the labeling precursor, 1-(N-(t-butoxycarbonyl)amino)-3-[((trifluoromethyl)sulfonyl)oxy]-cyclobutane-1-carboxylic acid ethyl ester, may be dissolved in an inert organic solvent before it is added to the mixture.

Various solvents that do not have reactivity with the [$^{18}$F] fluoride ion, the phase transfer catalyst, the potassium ion, and the labeling precursor compound are usable as the inert organic solvent used in the radiofluorination step; and preferably, a solvent selected from the group consisting of tetrahydrofuran, 1,4-dioxane, acetone, dimethylformamide, dimethylsulfoxide, and acetonitrile can be used, with acetonitrile being particularly preferable. The amount of the inert organic solvent to be used is preferably adjusted so that the labeling precursor concentration in the reaction solution under the radiofluorination reaction is 40 mmol/L or more, in order to significantly improve the yield in the radiofluorination reaction.

Various conditions can be used as the reaction condition for the radiofluorination step; for example, a condition in which the reaction solution is heated while stirring can be used. The heating temperature in this case is preferably not higher than the boiling temperature of the inert organic solvent added to the reaction solution; for example, when acetonitrile is used as the inert organic solvent, the heating temperature can be from 70 to 90° C. The reaction time depends on the reaction temperature; when, for example, the reaction temperature is 83° C., a sufficient reaction time is 3 minutes or longer. The longer the reaction time is, the further the radioactive fluorine-labeling reaction is expected to proceed, but care must be taken because the decay of the radioactive fluorine proceeds simultaneously.

After the radiofluorination step has been completed, the deesterification step is performed to produce [$^{18}$F]1-(N-(t-butoxycarbonyl)amino)-3-fluorocyclobutane-1-carboxylic acid (hereinafter referred to as "[$^{18}$F]DE-Boc-FACBC"). The present invention is characterized in that the deesterification reaction in this step is performed in a solid-phase column. In the most preferred embodiment, the sample to be deesterified, i.e., [$^{18}$F]Boc-FACBC, is trapped on the solid-phase column by diluting a reaction solution containing [$^{18}$F]Boc-FACBC obtained in the radiofluorination step with water, and passing the resulting solution as a sample through a solid-phase column. Dilution of the reaction solution is performed to prevent [$^{18}$F]Boc-FACBC from eluting without being trapped on the column when the sample is passed through the solid-phase column. Therefore, the water used for dilution may be used in an amount sufficient to trap [$^{18}$F]Boc-FACBC on the packing of the solid-phase column; when the solvent of the reaction solution is acetonitrile, a sufficient amount of water is five times the amount of the solvent.

The solid-phase column used in the deesterification step must be a solid-phase column filled with reverse-phase packing. Preferably, the column packing is one having a hydrophobic functional group such as phenyl, cyclohexyl and alkyl groups; and more preferably, one having a structure with a support to which $C_2$-$C_{18}$ alkyl groups are attached via silicon. In the most preferred embodiment, a column filled with packing having octadecylsilyl groups as functional groups can be used. Moreover, it is preferable to use a column packing having a structure in which the functional groups are difficult to be detached from the support under aqueous reaction conditions and during a long-term deesterification reaction.

After the sample has been trapped on the solid-phase column, the column is charged with an alkaline solution. In the most preferred embodiment, an alkaline solution is charged by directly introducing the alkaline solution into the column, stopping the feed of the alkaline solution after confirming that the alkaline solution has begun to leak through the outlet of the column, and sealing the outlet of the column. Examples of the alkali used here include sodium hydroxide and potassium hydroxide, with sodium hydroxide being preferable considering that the target product of the invention is used as an injection.

In the most preferred embodiment, the volume of the alkaline solution is about equal to the volume of the column. In this instance, care must be taken because if the volume of the alkaline solution to be used is excessive, the previously deesterified sample may be discharged together with the waste solution, thereby causing the yield to decrease.

The concentration of the alkaline solution to be used is not limited as long as the alkali can be introduced into the column in an amount sufficient to perform deesterification. The concentration of the alkaline solution is determined in consideration of a usable volume of the alkaline solution and a necessary amount of the alkali. In this instance, care must be taken because if an excessive amount of alkali is used, it will be necessary to use a larger amount of acid for neutralization in the subsequent deprotection step.

After the solid-phase column has been charged with the alkaline solution, the column is kept standing still for a certain period of time so as to effect deesterification of the sample in the column. In this instance, the temperature of the column need not be specifically controlled, but the operation can be performed at room temperature. The duration for which the column is kept standing still may be a period of time sufficient to perform deesterification. The longer the duration is, the further the deesterification reaction will proceed, but care must be taken because the decay of the radioactive fluorine proceeds simultaneously. For example, when [$^{18}$F]Boc-FACBC is retained in an ODS column containing 400 mg of resin, and 0.8 mL of 4 mol/L sodium hydroxide solution is injected into the column to perform deesterification, a time period of from 1 to 5 minutes is sufficient.

After the completion of deesterification, the outlet of the column is opened, thereby causing [$^{18}$F]DE-Boc-FACBC obtained by the deesterification to be discharged together with the alkaline solution. After the alkaline solution has been discharged, an alkaline solution may be further added to the column, followed by repeating the same operation as above, so that [$^{18}$F]Boc-FACBC remaining in the reverse-phase column can be more thoroughly deesterified, thereby improving the yield. It is preferable that, after the discharge, the column is subsequently flushed with water so as to discharge residual [$^{18}$F]DE-Boc-FACBC from the column, thereby further improving the yield.

After the completion of the deesterification step, the deprotection step is performed to deprotect the amino-protecting group, thereby yielding [$^{18}$F]FACBC which is the target product of the present invention. The deprotection step can be performed according to a known method, for example, a method described in the literature "J. McConathy et al., Applied Radiation and Isotopes, 2003, 58, p. 657-666". In a preferred embodiment, the deprotection step can be performed by imparting an acidic condition to a reaction solution containing [$^{18}$F]DE-Boc-FACBC. The acidic condition can be imparted by various methods, for example, a method in which an acid is added to a solution containing [$^{18}$F]DE-Boc-FACBC. The acid to be used here is not particularly limited, but preferably includes an acid selected from inorganic acids such as hydrochloric acid, sulfuric acid and nitric acid, and organic acids such as perfluoroalkyl carboxylic acid (for example, trifluoroacetic acid). The amount of the acid to be added should be sufficient to render the pH of the solution containing [$^{18}$F]DE-Boc-FACBC to be 1 or less. Specifically, the amount of the acid should be such that the alkali in the [$^{18}$F]DE-Boc-FACBC solution obtained in the deesterification step is neutralized, and a sufficient acidic condition is imparted to the sample solution. For example, when [$^{18}$F]Boc-FACBC is subjected to the deesterification repeated twice using 0.8 mL of 4 mol/L sodium hydroxide solution, 2.2 mL of 6 mol/L hydrochloric acid may be added to the eluted reaction solution. In the deprotection step, the reaction solution is preferably heated to allow the reaction to proceed more rapidly. The reaction time depends on the reaction temperature or other conditions, but when the deprotection reaction under the above-described conditions is performed at 60° C., a sufficient reaction time is 5 minutes. The [$^{18}$F]FACBC solution obtained in the deprotection step may be optionally purified using an ion retardation column, an alumina column, or a reverse-phase column.

EXAMPLES

Hereinafter, the present invention will be described in greater detail by way of Examples and Comparative Examples; however, the invention is not limited by these Examples.

Reference Example 1

Synthesis of syn-1-(N-(t-butoxycarbonyl)amino)-3-[((trifluoromethyl)sulfonyl)oxy]-cyclobutane-1-carboxylic acid Ethyl Ester Hydrolysis of Syn-Hydantoin (FIG. 1, Step 1)

250 mL of saturated aqueous barium hydroxide solution was added to 6.15 g (corresponding to 25 mmol) of syn-5-(3-benzyloxycyclobutane)hydantoin, and the mixture was refluxed while heating in an oil bath at 114° C. for 24 hours or more. Then, TLC analysis was performed using, as mobile solvents, two kinds of systems, i.e., chloroform:methanol=5:1 (Rf value of syn-hydantoin=around 0.6) and chloroform:methanol=95:1 (Rf value of syn-hydantoin=around 0.3), and the completion of the reaction was confirmed (based on coloration with UV and phosphomolybdic acid).

After confirming that the reaction had been completed, the resulting reaction solution was cooled to room temperature, and about 24 mL of 1 mol/mL sulfuric acid was added to neutralize the reaction solution. After the neutralization, the reaction solution was further stirred at room temperature for 5 minutes, and the resulting precipitate was filtered off. Then, the filtrate was concentrated to yield 5.67 g of syn-1-amino-3-benzyloxycyclobutane-1-carboxylic acid as white crystals.

Ethyl Esterification (FIG. 1, Step 2)

5.67 g of syn-1-amino-3-benzyloxycyclobutane-1-carboxylic acid, which had been fully dried to remove water, was dissolved in 200 mL of ethanol. To this solution, 9.5 mL (corresponding to 75 mmol) of triethylamine was added, and the mixture was cooled at −78° C. for 20 minutes, followed by addition of 4.6 mL (corresponding to 62.5 mmol) of thionyl chloride thereto. The reaction solution was stirred at 0° C. for 1 hour and at room temperature for 1 hour, followed by heating under reflux in an oil bath at 95° C. overnight. Then, the completion of the reaction was confirmed by TLC analysis that was performed using, as a mobile solvent, chloroform:methanol=95:1 (Rf value of the target product=around 0.6) (in which confirmation was made based on coloration with UV and phosphomolybdic acid). After confirming that the reaction had been completed, the resulting reaction solution was concentrated under reduced pressure to yield 7.64 g of syn-1-amino-3-benzyloxycyclobutane-1-carboxylic acid ethyl ester as white crystals.

Addition of Boc (FIG. 1, Step 3)

7.64 g of syn-1-amino-3-benzyloxycyclobutane-1-carboxylic acid ethyl ester was dissolved in 250 mL of a mixed solution of ethanol:triethylamine=9:1. The resulting solution was cooled in an ice bath for 15 minutes, and then 8.6 mL (corresponding to 37.5 mmol) of di-tert-butyl dicarbonate was added thereto, and the mixture was stirred at room temperature overnight. Then, the completion of the reaction was confirmed by TLC analysis that was performed using, as a mobile solvent, hexane:ethyl acetate=1:1 (Rf value of the target product=around 0.6) (in which confirmation was made based on coloration with UV and molybdophosphoric acid). After confirming that the reaction had been completed, the resulting reaction solution was concentrated under reduced pressure to yield white crystals as a residue. 150 mL of cold ethyl acetate and 150 mL of 0.5 mol/L cold hydrochloric acid were added to the residue, and the mixture was stirred at room temperature for 5 minutes and subsequently allowed to stand for separation. The organic layer was extracted and washed with 150 mL of water twice, with 150 mL of a saturated aqueous solution of sodium hydrogencarbonate, with 150 mL of water twice and 150 mL of saturated saline solution twice in this order, and the extract was dried with anhydrous sodium sulfate, and subsequently concentrated under reduced pressure to give yellow oily matter. Separately, the water layer was extracted and washed with 150 mL of ethyl acetate twice, with 150 mL of water twice and with 150 mL of saturated saline solution in this order, and the extract was dried with anhydrous sodium sulfate and then concentrated under reduced pressure, thereby collecting a small amount of yellow oily matter. The series of operations gave 8.82 g of light yellow oily matter. The residue was separated and purified by silica gel column chromatography (hexane:ethyl acetate=1:1) to yield 8.04 g (corresponding to 23 mmol) of syn-1-(N-(t-butoxycarbonyl)amino)-3-benzyloxy-cyclobutane-1-carboxylic acid ethyl ester as white crystals.

Debenzylation (FIG. 2, Step 4)

150 mL of ethanol was added to 8.04 g (corresponding to 23 mmol) of syn-1-(N-(t-butoxycarbonyl)amino)-3-benzyloxy-cyclobutane-1-carboxylic acid ethyl ester, and then 960 mg of palladium-on-activated carbon (10% palladium) was added thereto, purged with hydrogen, and the mixture was stirred at room temperature overnight. After the reaction, the palladium-on-activated carbon was filtered off using Celite, and the resulting filtrate was concentrated under reduced pressure to give 5.74 g of white crystals as a residue. The reaction was traced by TLC analysis using, as a mobile solvent, hexane:ethyl acetate=1:1 (Rf value of the target reaction product=around 0.2) (confirmed based on coloration with UV and ninhydrin) to confirm the completion of the reaction. Then, the residue was separated and purified by silica gel column chromatography (hexane:ethyl acetate=1:1, hexane:ethyl acetate=4:1) to yield 5.36 g (corresponding to 20.7 mmol) of syn-1-(N-(t-butoxycarbonyl)amino)-3-hydroxy-cyclobutane-1-carboxylic acid ethyl ester as white crystals.

Triflation (FIG. 3, Step 5)

2.07 g (8 mmol) of syn-1-(N-(t-butoxycarbonyl)amino)-3-hydroxy-cyclobutane-1-carboxylic acid ethyl ester was dissolved in 26 mL of pyridine, and the solution was stirred in an ice bath for 20 minutes. 2.0 mL (corresponding to 12 mmol) of anhydrous trifluoromethanesulfonic acid was added thereto, and the mixture was stirred as it was for 30 minutes. The reaction was traced by TLC analysis using, as a mobile solvent, hexane:diethyl ether=1:1 (Rf value of the target reaction product=around 0.6) (confirmed based on coloration with ninhydrin) to confirm the completion of the reaction. After confirming that the reaction had been completed, 100 mL of water and 100 mL of ether were added to the reaction solution, and the resulting mixture was extracted and washed with 100 mL of 1 mol/L hydrochloric acid twice, with 100 mL of water twice and with 100 mL of saturated saline solution twice in this order. The resulting extract was dried with anhydrous sodium sulfate and then concentrated under reduced pressure to give 2.78 g of light yellow crystals. The reaction mixture was separated and purified by silica gel column chromatography (hexane:diethyl ether=3:1) to yield white crystals, and the resultant white crystals were again re-crystallized using pentane:diethyl ether to yield 1.84 g (corresponding to 4.7 mmol) of syn-1-(N-(t-butoxycarbonyl) amino)-3-[((trifluoromethyl)sulfonyl)oxy]-cyclobutane-1-carboxylic acid ethyl ester.

Comparative Example $H_2{}^{18}O$ containing [$^{18}F$] fluoride ions (13 to 182 GBq) was passed through an anion-exchange column, such that [$^{18}F$] fluoride ions were adsorbed and trapped on the column. A potassium carbonate solution was then passed through the column to elute [$^{18}F$] fluoride ions, and subsequently, the column was flushed with water and the wash solution was combined with the eluate. To the resulting solution was added an acetonitrile solution of 4,7,13,16,21,24-hexaoxa-1,10-diazabicyclo[8.8.8]hexacosane (trade name: Kryptofix 222, manufactured by Merck), and the mixture was heated and evaporated to dryness.

To the dried mixture was added a solution obtained by dissolving 32 mg of 1-(N-(t-butoxycarbonyl)amino)-3-[((trifluoromethyl)sulfonyl)oxy]-cyclobutane-1-carboxylic acid ethyl ester in 1 mL of acetonitrile, and the resulting mixture was stirred at 83° C. for 3 minutes so as to allow the radiofluorination reaction to proceed. The mixture was then allowed to cool at room temperature for 5 minutes, and 4 mL of diethyl ether was added thereto. The resulting mixture was passed through a Silica Sep-Pak (registered trademark of Waters Investments Limited or trade name, available from Nihon Waters K. K.) to give an acetonitrile/diethyl ether solution of [$^{18}F$]Boc-FACBC.

To the resulting acetonitrile/diethyl ether solution of [$^{18}F$]Boc-FACBC was added 1.5 mL of 4 mol/L hydrochloric acid, and the mixture was heated at 120° C. for 15 minutes to perform deprotection. The resulting product was subsequently purified by being passed through an ion retardation column (trade name: AG11A8, manufactured by Bio-Rad Laboratories Japan, Inc.), an alumina column (trade name: Sep-Pak (registered trademark, manufactured by Waters Investments Limited) light ALUMN, manufactured by Nihon Waters K. K.), and a reverse-phase column (trade name: Oasis HLB Plus EXTRACTION Cartridge Column, manufactured by Nihon Waters K. K.) in this order, to yield a [$^{18}F$]FACBC solution. The yield of the [$^{18}F$]FACBC solution was from 9.4 to 13.4 mL. The resulting [$^{18}F$]FACBC was subjected to TLC analysis under the following conditions, and the radiochemical purity was determined according to the following equation (1).

TLC Analysis Conditions:
  Mobile phase: acetonitrile/methanol/water/acetic acid=20/5/5/1
  TLC plate: Silica Gel 60F254 (trade name, film thickness: 0.25 mm, manufactured by Merck)
  Developing length: 10 cm
  TLC scanner: Rita Star (manufactured by Raytest)

$$\text{Radiochemical purity (\%)} = \frac{\text{Amount of radioactivity at the peak of } [^{18}F]FACBC}{\text{Total amount of radioactivity on the TLC plate}} \quad (1)$$

In addition, the amounts of non-radioactive impurities in the target product were compared using the values obtained by correcting, in accordance with the following equation (2), the peak area value of each impurity confirmed by HPLC analysis under the following conditions (hereinafter referred to as "corrected area values"). The sample solution subjected to HPLC analysis was suitably diluted using a physiological saline solution (dilution factor=2.1 to 9.9).

$$\text{Corrected area value} = \frac{\text{Area value of the peak of each impurity}}{\text{Amount of injected sample}} \times \text{Dilution factor} \times \text{Yield of } [^{18}F]FACBC \text{ solution} \quad (2)$$

HPLC Measurement Conditions:
  Column: CAPCELLPAK C18 MG (trade name, manufactured by Shiseido Co., Ltd., size: 5 μm, 4.6 mm I.D.×250 mm)
  Column temperature: room temperature (about 25° C.)
  Mobile phase: using 5 mmol/L sodium octanesulfonate-containing phosphate buffer (pH 2.1) as solution A, and acetonitrile as solution B, concentration gradient control was performed by varying the blending ratio of the solutions A and B as shown in Table 1.

TABLE 1

| Mobile phase in HPLC analysis | | |
|---|---|---|
| Time (min.) after injection | Mobile phase A (%) | Mobile phase B (%) |
| 0-10 | 95 → 90 | 5 → 10 |
| 10-40 | 90 | 10 |
| 40-41 | 90 → 95 | 10 → 5 |

Mobile phase flow rate: 1.0 mL/min
  Sample injection amount: 10 μL
  Post-column derivatization conditions:
  Reaction solution: 0.3 mol/L boric acid buffer (pH 10.4), 6 mmol/L o-phthalaldehyde, and 6 mmol/L N-acetyl-L-cysteine
  Reaction solution flow rate: 1.0 mL/min
  Reaction temperature: 50° C.
  Detector: fluorescence detector (type: Waters 2475 model (manufactured by Nihon Waters K. K.); excitation wavelength: 330 nm; fluorescence wavelength: 430 nm)

The experiment of Comparative Example was repeated 19 times.

The radiochemical purity of the resulting [$^{18}F$]FACBC was 98.8±0.4%. The peaks of the impurities confirmed on the HPLC chromatograms were defined as shown in Table 2. The corrected area value of the peak of each impurity was as shown in Table 3.

TABLE 2

| Name of each impurity | |
|---|---|
| Retention time (average value) (min.) | Name of impurity |
| 8.0 | A |
| 8.9 | B |
| 9.8 | C |
| 14.7 | D |
| 23.8 | E |
| 30.3 | F |
| 30.8 | G |
| 35.9 | H |

TABLE 3

Corrected area value of each impurity
Corrected area value/$10^8$

| A | B | C | D | E | F | G | H | Total |
|---|---|---|---|---|---|---|---|---|
| 515.6 | 63.0 | 40.2 | 1.6 | 226.3 | 26.6 | 44.1 | 40.7 | 986.8 |

Examples 1 and 2

$H_2{}^{18}O$ containing [$^{18}$F] fluoride ions (7 to 36 GBq) was passed through an anion-exchange column, such that [$^{18}$F] fluoride ions were adsorbed and trapped on the column. A potassium carbonate solution was then passed through the column to elute [$^{18}$F] fluoride ions, and subsequently, the column was flushed with water and the wash solution was combined with the eluate. To the resulting solution was added an acetonitrile solution of 4,7,13,16,21,24-hexaoxa-1,10-diazabicyclo[8.8.8]hexacosane (trade name: Kryptofix 222, manufactured by Merck), and the mixture was heated and evaporated to dryness.

To the dried mixture was added a solution obtained by dissolving 32 mg of 1-(N-(t-butoxycarbonyl)amino)-3-[((trifluoromethyl)sulfonyl)oxy]-cyclobutane-1-carboxylic acid ethyl ester in 1 mL of acetonitrile, and the resulting mixture was heated at 83° C. while stirring for 3 minutes.

The resulting reaction solution was allowed to cool at room temperature for 5 minutes and then diluted with 14 mL of water, and the resulting solution was passed through each Sep-Pak (registered trademark, Waters Investments Limited) cartridge (manufactured by Nihon Waters K. K.) shown in Table 4, and the column was further washed with 10 mL of water.

TABLE 4

Solid-phase column used in each Example

| | Solid-phase column (product name) |
|---|---|
| Example 1 | tC2 |
| Example 2 | tC18 |

The solid-phase column was dried by passing air therethrough, and then the column was charged with 0.8 mL of 4 mol/L sodium hydroxide solution, followed by sealing the outlet of the column. After elapse of 3 minutes, the outlet of the column was opened to elute the alkaline solution from the solid-phase column, and the eluate was collected in a vial. The column was further charged with 0.8 mL of 4 mol/L sodium hydroxide solution, and the same procedure as above was repeated. The solid-phase column was subsequently washed with 3 mL of water, and the wash solution was combined with the previously collected alkaline solution.

2.2 mL of 6 mol/L hydrochloric acid was added to the above collected solution, and deprotection reaction was performed at 60° C. for 5 minutes. The resulting product was subsequently purified by being passed through an ion retardation column (trade name: AG11A8, manufactured by Bio-Rad Laboratories Japan, Inc.), an alumina column (trade name: Sep-Pak (registered trademark, Waters Investments Limited) light ALUMN, manufactured by Nihon Waters K. K.), and a reverse-phase column (trade name: Oasis HLB Plus EXTRACTION Cartridge Column, manufactured by Nihon Waters K. K.) in this order, to yield a [$^{18}$F]FACBC solution. The yield of the [$^{18}$F]FACBC solutions was from 11.9 to 17.0 mL.

The obtained [$^{18}$F]FACBC solution was evaluated for the radiochemical purity of [$^{18}$F]FACBC and the corrected area value of each impurity under the same conditions as in Comparative Example. The sample solutions subjected to HPLC analysis were suitably diluted using a physiological saline solution (dilution factor=3.0 to 4.7).

The radiochemical purities of [$^{18}$F]FACBC produced in Examples 1 and 2 were 99.4 and 99.3%, respectively. Table 5 shows the corrected area value of the peak of each impurity. As shown in Table 5, in each of Examples 1 and 2, the amounts of all of the non-radioactive impurities except the impurity D were reduced, as compared with the sample produced according to a conventional process (Comparative Example 1), and the total of the corrected area values of all the impurities was reduced to less than half. These results confirmed that the amount of non-radioactive impurities can be reduced by the process of production of [$^{18}$F]FACBC according to the present invention.

TABLE 5

Corrected area value of each impurity
Corrected area value/$10^8$

| | A | B | C | D | E | F | G | H | Total |
|---|---|---|---|---|---|---|---|---|---|
| Ex. 1 | 203.5 | 6.2 | 4.0 | 19.7 | 9.3 | 0.5 | 4.9 | 3.2 | 257.7 |
| Ex. 2 | 218.7 | 5.4 | 8.3 | 38.2 | 5.2 | 2.0 | 4.4 | 1.6 | 292.6 |

INDUSTRIAL APPLICABILITY

The process for production of a radioactive fluorine-labeled organic compound according to the invention can be used in the field of manufacturing radiopharmaceuticals.

Figure 1:
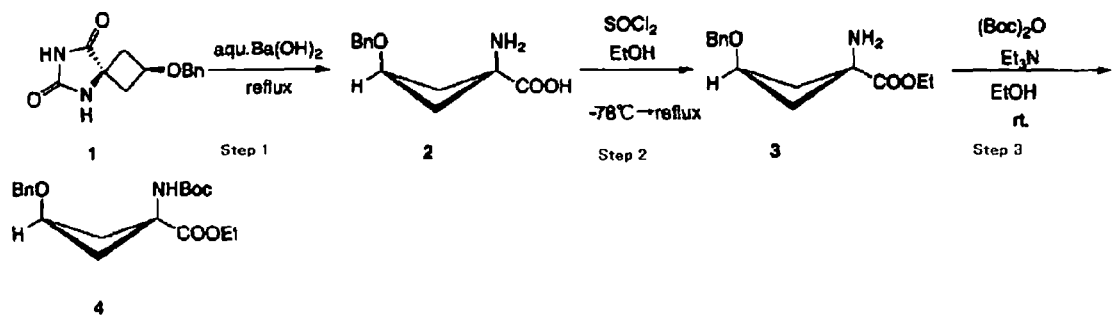
FIG. 1 is a synthetic scheme of syn-1-(N-(t-butoxycarbonyl)amino)-3-benzyloxy-cyclobutane-1-carboxylic acid ethyl ester.
Figure 2:
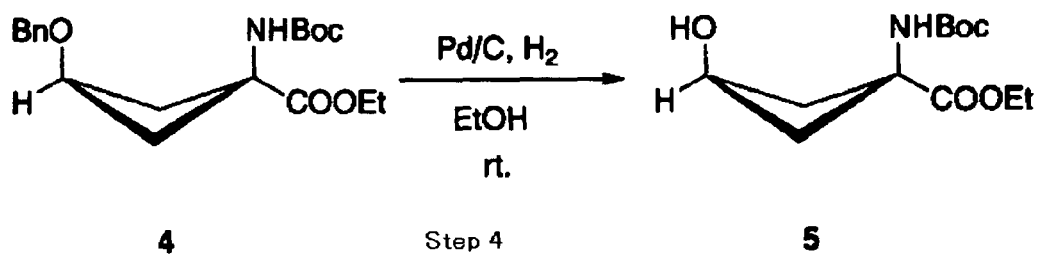
FIG. 2 is a synthetic scheme of syn-1-(N-(t-butoxycarbonyl)amino)-3-hydroxy-cyclobutane-1-carboxylic acid ethyl ester.
Figure 3:
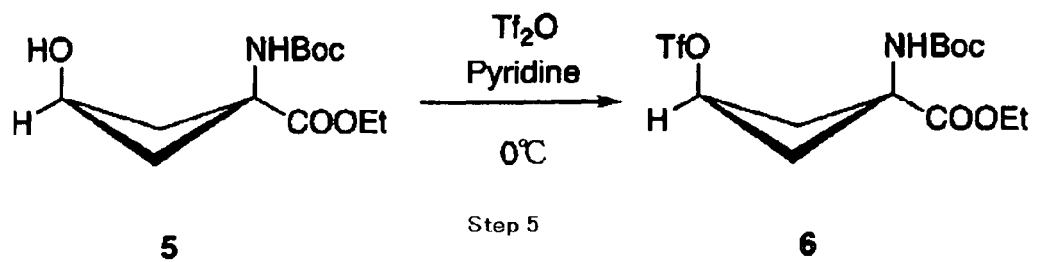
FIG. 3 is a synthetic scheme of syn-1-(N-(t-butoxycarbonyl)amino)-3-[((trifluoromethyl)sulfonyl)oxy]-cyclobutane-1-carboxylic acid ethyl ester.

The invention claimed is:

1. A process for production of a radioactive fluorine-labeled organic compound, which comprises:

a deesterification step of retaining, in a reverse-phase column, a compound represented by the following formula (1):

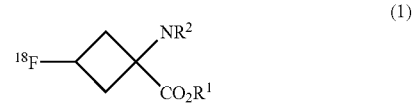

(1)

wherein $R^1$ is a linear or branched $C_1$-$C_{10}$-alkyl chain or an aromatic substituent, and $R^2$ is a protecting group;

charging the column with an alkaline solution to deesterify the above compound, and subsequently discharging the alkaline solution from the column to obtain a compound represented by the following formula (2):

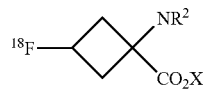

wherein X is a cation contained in the alkali used in the deesterifiction step; and
R² is a protecting group; and
a deprotection step of deprotecting the amino-protecting group of the compound obtained in the deesterification step to obtain a compound represented by the following formula (3):

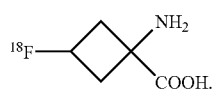

2. The process for production of a radioactive fluorine-labeled organic compound according to claim 1, wherein X in the formula (2) is sodium or potassium.

3. The process for production of a radioactive fluorine-labeled organic compound according to claim 2, wherein the alkali solution used in the deesterification step is a sodium hydroxide solution or potassium hydroxide solution.

4. The process for production of a radioactive fluorine-labeled organic compound according to claim 3, wherein the alkali solution used in the deesterification step is an aqueous sodium hydroxide solution.

5. The process for production of a radioactive fluorine-labeled organic compound according to any one of claims 1 to 4, wherein the reverse-phase column used in the deesterification step contains packing that has a structure in which a $C_1$-$C_{18}$-alkyl chain is attached to a support via silicon.

* * * * *